US008858559B2

(12) United States Patent  
Milburn et al.

(10) Patent No.: US 8,858,559 B2
(45) Date of Patent: Oct. 14, 2014

(54) SAW BLADE STABILITY AND COLLET SYSTEM MECHANISM

(75) Inventors: Thaddeus Scott Milburn, Fort Worth, TX (US); Bret Randal Hauser, Flower Mound, TX (US); R. Mitchell Sherry, Fort Worth, TX (US); S. Shane Dexter, Keller, TX (US)

(73) Assignee: Medtronic PS Medical, Inc., Fort Worth, TX (US)

( * ) Notice: Subject to any disclaimer, the term of this patent is extended or adjusted under 35 U.S.C. 154(b) by 201 days.

(21) Appl. No.: 13/366,621

(22) Filed: Feb. 6, 2012

(65) Prior Publication Data

US 2013/0204255 A1   Aug. 8, 2013

(51) Int. Cl.
*A61B 17/00*   (2006.01)

(52) U.S. Cl.
USPC ................................ 606/82; 606/177; 30/392

(58) Field of Classification Search
USPC ................. 606/176–177, 79, 82; 30/392–394
See application file for complete search history.

(56) References Cited

U.S. PATENT DOCUMENTS

| | | |
|---|---|---|
| 3,554,197 A | 1/1971 | Dobbie |
| 3,678,934 A | 7/1972 | Warfield et al. |
| 3,943,934 A | 3/1976 | Bent |
| 3,974,868 A | 8/1976 | Derbyshire |
| 4,020,555 A | 5/1977 | Hedrick |
| 4,106,181 A | 8/1978 | Mattchen |
| 4,386,609 A | 6/1983 | Mongeon |
| 4,513,742 A | 4/1985 | Arnegger |
| 4,584,999 A | 4/1986 | Arnegger |
| 4,617,930 A | 10/1986 | Saunders |
| 4,739,557 A | 4/1988 | Wagner |
| 4,819,334 A | 4/1989 | Mongeon |
| 4,846,161 A | 7/1989 | Roger |
| 4,985,031 A | 1/1991 | Buss et al. |
| 5,002,555 A | 3/1991 | Petersen |
| 5,092,869 A | 3/1992 | Waldron |
| 5,122,142 A | 6/1992 | Pascaloff |
| 5,133,728 A | 7/1992 | Petersen |
| 5,135,533 A | 8/1992 | Petersen et al. |
| 5,178,626 A | 1/1993 | Pappas |
| 5,201,749 A | 4/1993 | Sachse et al. |
| D337,160 S | 7/1993 | Evans |
| 5,237,884 A | 8/1993 | Seto |
| 5,263,972 A | 11/1993 | Evans et al. |
| 5,265,343 A | 11/1993 | Pascaloff |
| D343,247 S | 1/1994 | Walen |
| D346,318 S | 4/1994 | Evans |
| 5,306,285 A | 4/1994 | Miller et al. |

(Continued)

FOREIGN PATENT DOCUMENTS

| | | |
|---|---|---|
| DE | 4036904 | 5/1992 |
| EP | 0554929 | 8/1993 |
| EP | 0776634 | 6/1997 |
| WO | WO-9513020 | 5/1995 |

*Primary Examiner* — Andrew Yang
*Assistant Examiner* — Olivia C Chang
(74) *Attorney, Agent, or Firm* — Harness, Dickey

(57) ABSTRACT

A surgical system for cutting tissue of a patient includes an outer housing and a reciprocating assembly structurally configured to carry a cutting tool in a reciprocating motion. An actuator knob is manually accessible to the user and may be fixed axially to the outer housing. The reciprocating assembly may reciprocate relative to the actuator knob. The actuator knob may be configured for rotational movement between a lock position and an unlock position. The system may also include a locking mechanism configured to retain a cutting tool within the reciprocating assembly. The locking mechanism may be responsive to movement of the actuator knob to maintain the tool within the output shaft when the actuator knob is in the lock position and permit removal of the tool when the actuator knob is in the unlock position. Surgical cutting tools, such as blades include thickness enhancing features.

22 Claims, 10 Drawing Sheets

(56) References Cited

U.S. PATENT DOCUMENTS

| | | | |
|---|---|---|---|
| D348,194 S | 6/1994 | Tanis |
| D351,907 S | 10/1994 | Matthai et al. |
| 5,366,312 A | 11/1994 | Raines |
| 5,382,249 A | 1/1995 | Fletcher |
| 5,391,169 A | 2/1995 | McGuire |
| 5,403,318 A | 4/1995 | Boehringer et al. |
| 5,423,823 A | 6/1995 | Schmieding |
| 5,423,845 A | 6/1995 | McDaniel |
| D360,946 S | 8/1995 | Goris |
| D361,029 S | 8/1995 | Goris |
| 5,439,472 A | 8/1995 | Evans et al. |
| D362,065 S | 9/1995 | Goris |
| 5,449,360 A | 9/1995 | Schreiber |
| 5,468,247 A | 11/1995 | Matthai et al. |
| 5,470,335 A | 11/1995 | du Toit |
| 5,489,285 A | 2/1996 | Goris |
| 5,496,316 A | 3/1996 | Goris |
| 5,496,325 A | 3/1996 | McLees |
| 5,505,738 A | 4/1996 | Hempel et al. |
| 5,507,763 A | 4/1996 | Petersen et al. |
| 5,554,165 A | 9/1996 | Raitt et al. |
| 5,578,039 A | 11/1996 | Vendrely et al. |
| 5,591,170 A | 1/1997 | Spievack et al. |
| 5,601,565 A | 2/1997 | Huebner |
| 5,609,603 A | 3/1997 | Linden |
| 5,611,802 A | 3/1997 | Samuelson et al. |
| 5,658,304 A | 8/1997 | Lim |
| D385,163 S | 10/1997 | Hutchins et al. |
| D385,164 S | 10/1997 | Hutchins et al. |
| 5,676,680 A | 10/1997 | Lim |
| 5,694,693 A | 12/1997 | Hutchins et al. |
| 5,702,415 A | 12/1997 | Matthai et al. |
| 5,725,530 A | 3/1998 | Popken |
| 5,729,904 A | 3/1998 | Trott |
| 5,735,866 A | 4/1998 | Adams et al. |
| 5,810,822 A | 9/1998 | Mortier |
| 5,839,196 A | 11/1998 | Trott |
| D402,516 S | 12/1998 | Okada |
| 5,846,244 A | 12/1998 | Cripe |
| 5,848,473 A | 12/1998 | Brandenburg, Jr. |
| 5,848,474 A | 12/1998 | Kudo et al. |
| 5,851,209 A | 12/1998 | Kummer et al. |
| 5,916,218 A | 6/1999 | Hagen et al. |
| RE36,269 E * | 8/1999 | Wright .......................... 279/90 |
| D415,401 S | 10/1999 | Imboden et al. |
| 6,007,541 A | 12/1999 | Scott |
| D420,262 S | 2/2000 | Khachatoorian |
| 6,022,353 A | 2/2000 | Fletcher et al. |
| D427,865 S | 7/2000 | Mills, Jr. |
| 6,113,618 A | 9/2000 | Nic |
| 6,113,619 A | 9/2000 | Pascaloff |
| D439,666 S | 3/2001 | Ventura |
| D448,634 S | 10/2001 | Hickman |
| 6,302,406 B1 | 10/2001 | Ventura |
| D455,490 S | 4/2002 | Pascaloff |
| D459,172 S | 6/2002 | Bissell |
| D459,805 S | 7/2002 | Pascaloff |
| D465,138 S | 11/2002 | Raines |
| 6,485,495 B1 | 11/2002 | Jenkinson |
| 6,503,253 B1 | 1/2003 | Fisher et al. |
| D479,106 S | 9/2003 | Robertsson |
| D479,107 S | 9/2003 | Rack |
| D479,447 S | 9/2003 | Rack |
| 6,638,290 B2 | 10/2003 | Pascaloff et al. |
| D482,945 S | 12/2003 | Grolimund |
| 6,656,186 B2 | 12/2003 | Meckel |
| D484,759 S | 1/2004 | Rack |
| D485,140 S | 1/2004 | Rack |
| D485,141 S | 1/2004 | Rack |
| D485,142 S | 1/2004 | Rack |
| D485,479 S | 1/2004 | Rack |
| 6,684,481 B2 | 2/2004 | Kullmer |
| 6,689,139 B2 | 2/2004 | Horn |
| 6,723,101 B2 | 4/2004 | Fletcher et al. |
| D489,823 S | 5/2004 | Fisher et al. |
| 6,860,886 B1 | 3/2005 | Lee |
| 6,865,813 B2 | 3/2005 | Pollak |
| 6,875,222 B2 | 4/2005 | Long et al. |
| 6,896,679 B2 | 5/2005 | Danger et al. |
| 6,949,110 B2 | 9/2005 | Ark et al. |
| 7,001,403 B2 | 2/2006 | Hausmann et al. |
| 7,003,888 B2 | 2/2006 | Bigden et al. |
| 7,040,023 B2 | 5/2006 | Nemazi et al. |
| D525,707 S | 7/2006 | Kullmer et al. |
| 7,083,623 B2 | 8/2006 | Michelson |
| D536,791 S | 2/2007 | Eskridge et al. |
| 7,189,239 B2 | 3/2007 | Fisher et al. |
| 7,322,985 B2 | 1/2008 | Lee |
| D578,848 S | 10/2008 | Camacho |
| 7,497,860 B2 | 3/2009 | Carusillo et al. |
| D589,772 S | 4/2009 | Ping |
| 7,527,628 B2 | 5/2009 | Fletcher et al. |
| D603,231 S | 11/2009 | Fisher et al. |
| 7,666,186 B2 | 2/2010 | Harp |
| 7,686,811 B2 | 3/2010 | Byrd et al. |
| 2002/0068952 A1 | 6/2002 | Pascaloff et al. |
| 2002/0116023 A1 | 8/2002 | Fletcher et al. |
| 2002/0133185 A1 | 9/2002 | Danger et al. |
| 2002/0133186 A1 | 9/2002 | Kullmer |
| 2002/0198556 A1 | 12/2002 | Ark et al. |
| 2003/0014067 A1 | 1/2003 | Kullman et al. |
| 2003/0032971 A1 | 2/2003 | Hausmann et al. |
| 2003/0158558 A1 | 8/2003 | Horn |
| 2003/0199880 A1 | 10/2003 | Meckel |
| 2004/0024405 A1 | 2/2004 | Lee |
| 2004/0098000 A1 | 5/2004 | Kleinwaechter |
| 2004/0098870 A1 * | 5/2004 | Nemazi et al. .................. 30/392 |
| 2004/0138668 A1 | 7/2004 | Fisher et al. |
| 2004/0138669 A1 | 7/2004 | Horn |
| 2004/0199167 A1 | 10/2004 | Fletcher et al. |
| 2004/0204731 A1 | 10/2004 | Gant |
| 2004/0243136 A1 | 12/2004 | Gupta et al. |
| 2005/0033275 A1 | 2/2005 | Hoegerle et al. |
| 2005/0065530 A1 | 3/2005 | Stauch et al. |
| 2005/0075642 A1 | 4/2005 | Felt et al. |
| 2005/0149041 A1 | 7/2005 | McGinley et al. |
| 2005/0192585 A1 | 9/2005 | Simmons |
| 2005/0245935 A1 | 11/2005 | Casey et al. |
| 2005/0273110 A1 | 12/2005 | Boehm et al. |
| 2006/0009796 A1 | 1/2006 | Carusillo et al. |
| 2006/0015117 A1 | 1/2006 | Haines |
| 2006/0058806 A1 | 3/2006 | Collazo |
| 2006/0200152 A1 | 9/2006 | Karubian et al. |
| 2006/0217729 A1 | 9/2006 | Eskridge et al. |
| 2006/0259055 A1 | 11/2006 | Thorne et al. |
| 2006/0282108 A1 | 12/2006 | Tanner |
| 2007/0016238 A1 | 1/2007 | Marietta |
| 2007/0055262 A1 | 3/2007 | Tomita et al. |
| 2007/0073303 A1 | 3/2007 | Namba |
| 2007/0083209 A1 | 4/2007 | Schenberger et al. |
| 2007/0118140 A1 | 5/2007 | Baur et al. |
| 2007/0123893 A1 | 5/2007 | O'Donoghue |
| 2007/0156160 A1 | 7/2007 | Petersen |
| 2007/0213692 A1 | 9/2007 | Millahn et al. |
| 2008/0027449 A1 | 1/2008 | Gundlapalli et al. |
| 2008/0119860 A1 | 5/2008 | McCarthy |
| 2008/0243125 A1 | 10/2008 | Guzman et al. |
| 2008/0312658 A1 | 12/2008 | Namba |
| 2009/0076513 A1 | 3/2009 | Szanto |
| 2009/0088758 A1 | 4/2009 | Bennett |
| 2009/0093814 A1 | 4/2009 | Fletcher et al. |
| 2009/0093815 A1 | 4/2009 | Fletcher et al. |
| 2009/0138017 A1 | 5/2009 | Carusillo et al. |
| 2009/0182338 A1 | 7/2009 | Walen et al. |
| 2009/0277022 A1 * | 11/2009 | Limberg et al. ................ 30/392 |
| 2009/0281546 A1 | 11/2009 | Collazo |
| 2009/0312761 A1 | 12/2009 | Boykin et al. |
| 2009/0312779 A1 | 12/2009 | Boykin et al. |
| 2009/0320299 A1 | 12/2009 | Kuhn et al. |
| 2009/0326540 A1 | 12/2009 | Estes |
| 2010/0069909 A1 | 3/2010 | Taylor |

* cited by examiner

SAW BLADE STABILITY AND COLLET SYSTEM MECHANISM

FIELD OF THE INVENTION

This disclosure is directed to a surgical system for cutting tissue and more particularly, to a blade stability and collet mechanism for a surgical saw and associated blades for cutting bone and tissue.

BACKGROUND

Surgical saw blades of varying sizes, shapes and thicknesses are inserted and removed from surgical saws prior to, sometimes during, and after surgical procedures and must be retained securely to the saw's reciprocating shaft. The variety of available blade types and sizes present challenges that must be overcome to maintain stability of the interface for all blade options as well as to maintain user simplicity for improved operational effectiveness. The saws are often arranged so that the saw blades project axially from the distal end of the saw with a blade retention post or driver positioned laterally within the saw. To accommodate the post, some blades have openings or gaps formed into their proximal ends. For operator simplicity, a saw design is often created to allow use of the various blade embodiments. However, when blades of differing geometry are used (thinner for example), the stability of the saw interface may not be as desirable as with thicker blades due to the increased clearances unless considerations are made in the design of the saw, blade or both. Further, the flexible design must be simple for the user to operate to minimize confusion and improve efficiency in the potentially busy environment of an operating room.

The present disclosure is directed to a surgical system including a blade retention mechanism and a saw blade addressing one or more of the limitations in the prior art.

SUMMARY OF THE INVENTION

In one exemplary aspect the present disclosure is directed to a surgical system for cutting bone and tissue of a patient. It includes an outer housing and a reciprocating assembly disposed in the outer housing. The reciprocating assembly may be structurally configured to carry a cutting tool in a reciprocating motion, and may have a tool receiving opening formed therein. An actuator knob is manually accessible to the user and may be fixed axially to the outer housing. The reciprocating assembly may reciprocate relative to the actuator knob. The actuator knob may be configured for rotational movement between a lock position and an unlock position. The system may also include a locking mechanism configured to retain a cutting tool within the reciprocating assembly. The locking mechanism may be responsive to movement of the actuator knob to maintain the tool within the output shaft when the actuator knob is in the lock position and permit removal of the tool when the actuator knob is in the unlock position.

In one aspect, the locking mechanism comprises a lock pin associated with the reciprocating assembly. The lock pin may be moveable in a direction transverse to the direction of the reciprocating motion when the actuator knob rotates between a lock position and an unlock position. In one aspect, the actuator knob comprises an inner cam surface configured to engage and displace the lock pin upon rotation of the actuator knob.

In another exemplary aspect the present disclosure is directed to a surgical system for cutting bone and tissue of a patient. The system includes a outer housing and a reciprocating assembly disposed in the outer housing. The reciprocating assembly may be structurally configured to carry a cutting tool in a reciprocating motion. The reciprocating assembly may have a tool receiving opening formed therein, and may comprise a locking mechanism configured to retain a cutting tool within the output shaft. The locking mechanism may be displaceable in a direction transverse to the direction of the reciprocating motion and may be structurally configured to engage the tool in a first position and to be disengaged from the tool in a second position. An actuator knob may be manually accessible to the user and may be disposed about the reciprocating assembly. The actuator knob may be fixed axially to the housing and may be rotatable relative to the housing. It may have an inner cam surface configured to selectively engage the locking mechanism and displace the locking mechanism from the first position to the second position. The inner cam surface may extend axially in the longitudinal direction to accommodate the reciprocating motion of the locking mechanism.

In one aspect, the locking mechanism includes a lock pin having a first portion configured to engage with the inner cam surface of the actuator knob, a second portion configured to engage a side of a cutting tool disposed within the tool receiving opening of the reciprocating assembly, and a neck portion disposed between the first and second portions. The neck portion may have a transverse width smaller than a transverse width of the second portion to permit insertion, retention and removal of the tool.

In another exemplary aspect, the present disclosure is directed to a surgical cutting blade for cutting bone material when the blade is coupled to a hand-held surgical saw. The cutting blade may include a distal portion comprising a plurality of cutting teeth, a proximal portion disposed opposite the distal portion shaped to attach to the surgical saw and being formed of a material having an upper surface and an opposing lower surface, the material having a first thickness. In addition, the blade may include intermittent thickness enhancing features on the proximal portion. The thickness enhancing features may have a high point offset from the upper surface and a low point offset from the lower surface of the material, the distance between the high point and low point forming a second thickness greater than the first thickness.

In one aspect, the intermittent thickness enhancing features comprises deformed portions formed by bends in the material. In another aspect, the deformed portions are at least one of embossments, extending fingers, and molded material. In one aspect, the intermittent thickness enhancing features are formed along lateral edges of the proximal portion.

In another exemplary aspect, the present disclosure is directed to a surgical cutting blade for cutting bone material when the blade is coupled to a hand-held surgical saw. The cutting blade may include a first surface comprising a first substantially planar surface portion and a first deformed surface portion. It may also include a second surface comprising a second substantially planar surface portion parallel to the first substantially planar surface portion and a second deformed surface portion. The distance between the first substantially planar surface portion and the second substantially planar surface portion may define a first thickness. The first deformed surface portion may have a first peak surface point offset from the first substantially planar surface, where the distance between the first peak surface point and the second surface define a second thickness greater than the first thickness. A plurality of cutting teeth may be disposed at an edge of the first and second planar surfaces.

In one aspect, the second deformed surface portion has a second peak surface point offset from the second substantially planar surface, and the distance between the first peak surface point and the second peak surface point defines the second thickness greater than the first thickness. In one aspect, the blade includes a distal portion including the plurality of cutting teeth, a proximal portion, and shank between the distal and proximal portions. The proximal portion may comprise both the first and second substantially planar surface portions and the first and second deformed surface portions.

BRIEF DESCRIPTION OF THE DRAWINGS

A more complete understanding of the present disclosure and advantages thereof may be acquired by referring to the following description taken in conjunction with the accompanying figures.

DETAILED DESCRIPTION

Reference is now made in detail to exemplary embodiments of the invention, examples of which are illustrated in the accompanying drawings. Wherever possible, the same reference numbers are used throughout the drawings to refer to the same or like parts.

Generally, the present disclosure relates to a bone cutting surgical system including a hand-held, high-speed, bone-cutting surgical saw and a cutting tool shown as a cutting saw blade. The surgical saw includes a mechanism that uniquely retains the cutting tool. In one aspect, it includes an intuitive quarter-turn actuator knob that is non-reciprocating. Because the actuator knob is non-reciprocating, it may shield users from inadvertent contact with the reciprocating portion of the saw. In addition, the quarter-turn knob may simplify the user interaction required to attach a cutting tool, which may provide benefits in a fast-paced environment of an operating room. The reciprocating saw shaft is arranged to accept both flat and shafted cutting tool shanks in varying thickness ranges. For thinner blades, thickness enhancing features such as one or more deformations or other features, are incorporated providing identical stability inherent with thicker flat blades.

Figure 1:
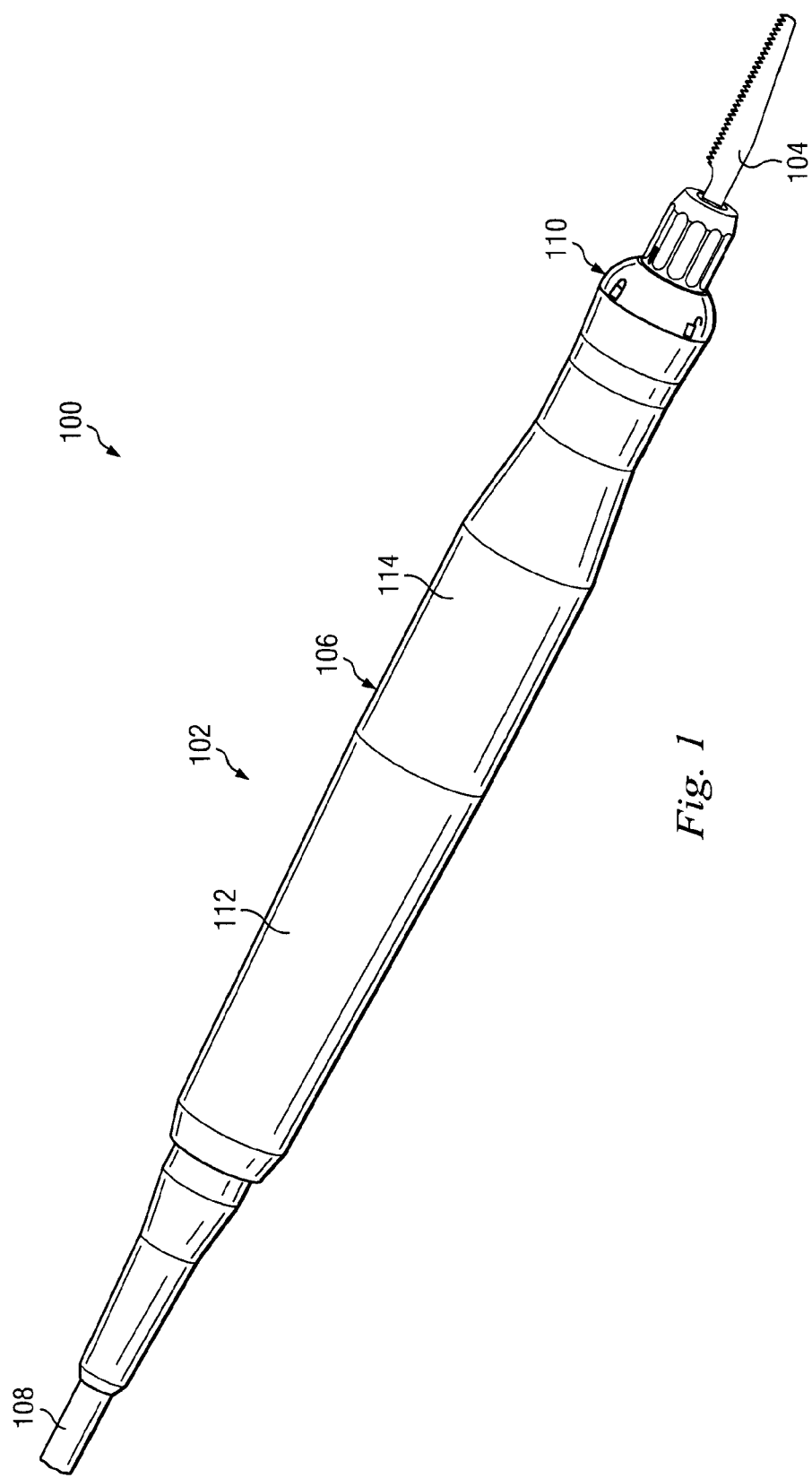
FIG. 1 is an illustration of an exemplary reciprocating bone-cutting surgical system according to one exemplary aspect of the present disclosure.

Turning now to FIG. 1, the present disclosure is directed to a bone-cutting surgical system 100 including a hand-held surgical saw 102 and a selectively removable micro-cutting tool 104, shown as a saw blade. The surgical saw 102 includes a hand-piece 106, a cord 108 extending from a proximal end, and a blade retaining mechanism 110 disposed at its distal end. The handpiece 106, in this example, is divided into a motor housing 112 and a drive housing 114. The motor housing 112 carries the motor that drives the reciprocating action of the cutting tool 104. The drive housing 114 carries the components that transform the rotating motor output to reciprocating motion and that drives the cutting tool 104. In one example, the cord 108 extends to a separate console (not shown) and may be permanently coupled or removably coupled to the power source. Additional contemplated embodiments include a power source as a part of the hand-piece 106, such as a battery powered hand-piece. In one example, the surgical saw is a pneumatically driven saw.

Figure 2:
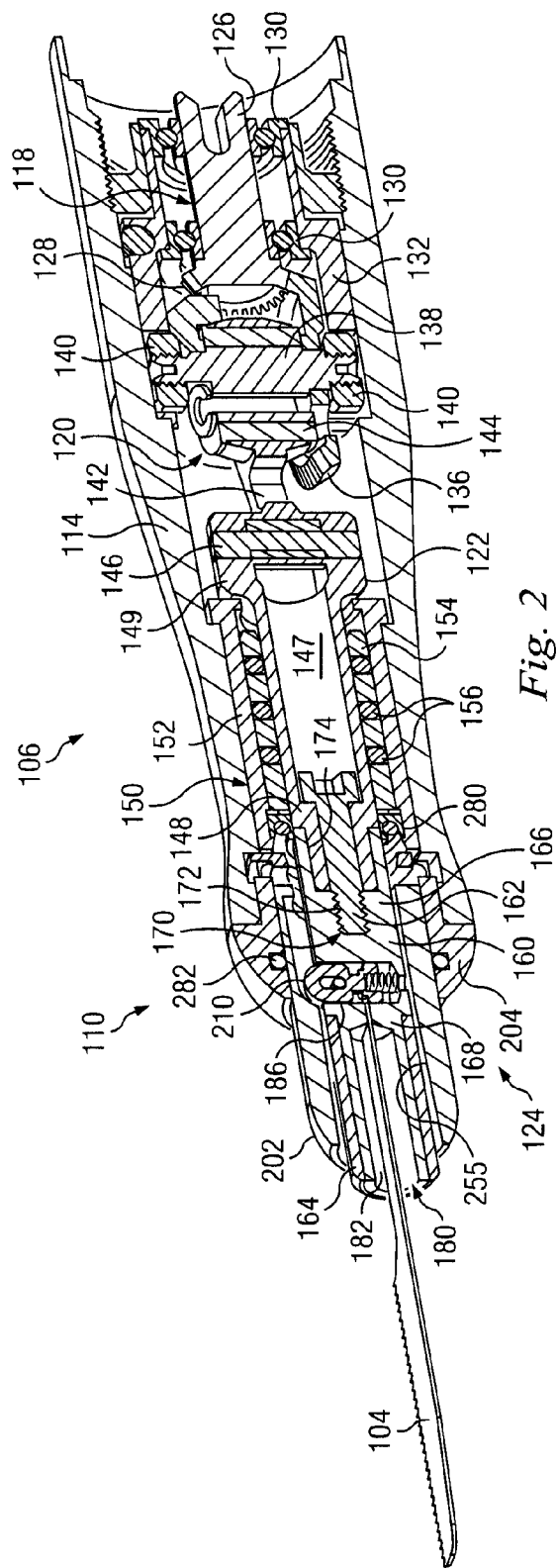
FIG. 2 is an illustration of a longitudinal cross-section of the reciprocating bone-cutting surgical system of FIG. 1 according to one exemplary aspect of the present disclosure.

FIG. 2 is an enlarged cutaway, cross-sectional view of the drive housing 114 of the handpiece 106 and the blade relating mechanism 110, with the cutting tool 104. The drive housing 114, according to an exemplary embodiment, includes a bevel pinion 118, an eccentric crank assembly 120, a yoke 122, and an output shaft assembly 124. The bevel pinion 118 includes a gear shaft 126 and a gear head 128. The gear shaft 126 is carried by bearings 130 in a bearing housing 132 disposed in the drive housing 114. The gear shaft 126 extends proximally and is configured to attach to a drive shaft of the motor (not shown) disposed in the motor housing 112 (FIG. 1).

The eccentric crank assembly 120 includes a bevel gear 136, a crank axle 138, bearings 140, and a crank arm 142. The bevel gear 136 mates with the gear head 128 of the bevel gear 118. The crank axle 138 is rotationally fixed to the bevel gear 136 so that rotation of the bevel gear results in rotation of the crank axle 138. The bearings 140 support ends of the crank axle 138 and maintain it in position. The crank axle 138 includes an eccentric portion 144, and the crank arm 142 extends from the crank axle 138. In use, the motor output shaft drives the gear shaft 126 of the bevel pinion 118. Rotation of the bevel pinion 118 rotates the bevel gear 136, converting the rotation about the longitudinal axis of the saw 102 to rotation about an axis transverse to the longitudinal axis. The bevel gear 136 drives the crank axle 138. As the crank axle 138 turns, the eccentric portion 144 rotates about the transverse axis. The crank arm 142, rotationally attached to the eccentric crank and is then reciprocated in a direction along the longitudinal axis.

The yoke 122 is connected to the crank arm 142 by a transversely extending connector pin 146. The yoke 122 includes a hollow longitudinal chamber 147 extending from a distal end 148 to a proximal end 149. The proximal end 149 is formed to receive the pin 146, which is rotatable relative to one or both of the crank arm 142 and the yoke 122. The yoke 122 is disposed within a linear bearing 150 carried in the drive housing 114. The linear bearing 150 includes a liner 152 fit within the drive housing 114 that carries a liner cage 154 and ball bearings 156. As the crank arm 142 moves in a reciprocating motion, the yoke 122 reciprocates in the linear bearing 150.

The output shaft assembly 124 includes an output shaft 160, a connector 162 connecting the output shaft 160 to the yoke 122, and a retaining sleeve 164 disposed about a portion of the output shaft 160. The output shaft 160 includes a proximal portion 166 and a distal portion 168. In the example shown, the proximal portion 166 includes a hollow receiving chamber 170 formed as a blind bore 172 with a countersink portion 174. The countersink portion 174 is configured to receive and interface with a distal end of the yoke 122. In one embodiment, these are press-fit together. The blind bore 172 receives the distal end 148 of the yoke 122. In this example, the blind bore portion of the receiving chamber 170 is threaded. In this example, a connector 162 extends from inside the hollow chamber 147 of the yoke 122 to connect with the output shaft 160, thereby fixedly securing them together. In this example, the connector 162 is a fastening bolt that extends from a location inside the hollow chamber 147 to the blind bore 172, and threads into the blind bore 172 to connect the output shaft 160 and the yoke 122. Thus, reciprocating movement of the yoke 122 results in reciprocating movement of the output shaft 160.

The distal portion 168 of the output shaft 160 includes a tool receiving opening 180 extending longitudinally into the saw 102. The tool receiving opening 180 is sized and configured to receive a cutting tool usable in a surgical procedure. In this example, the tool receiving opening 180 is sized and configured to receive the cutting tool 104. The tool receiving opening 180 in this embodiment is configured to receive either a flat shank of a cutting tool or a cylindrical shank of a cutting tool. To do this, the output shaft 160 has a central cylindrical bore 182 sized to receive and hold a cylindrical shaft of a cutting tool. In addition to the central cylindrical bore 182, the output shaft 160 includes two longitudinal slots 184 (not visible in FIG. 2) on opposing sides of the bore 182 that carry the cutting tool 104. The slots 184 can be seen particularly well in the cross-section of FIG. 5. These slots 184 are sized to receive a flat shank of a cutting tool, such as the cutting tool 104, that has a width greater than the diameter of the central cylindrical bore 182. Accordingly, the surgical saw 102 is configured to receive either type of tool without requiring interchanging of receiving components. This makes the surgical saw 100 compatible with a greater number of tools, simplifying tool changeover and resulting in fewer required tools in the surgical room. In the embodiment shown, the slots 184 extend in the proximal direction further than the cylindrical bore 182.

The output shaft 160 includes a transverse hole 186 configured to receive a portion of the blade retaining mechanism 110. The transverse hole 186 extends more than half-way through the output shaft diameter and through the slots 184.

The retaining sleeve 164 is disposed about the distal portion 168 of the output shaft 160. It does not cover the transverse hole 186 for reasons that will become apparent below. Since the slots 184 extend to the outer circumference of the output shaft, the retaining sleeve 164 serves as a boundary that limits the overall width of the cutting tool size that can be inserted into the slots 184. In addition, it limits transverse displacement and reacts transverse loading on flat cutting tools, such as blades. Transverse loading of tools with a cylindrical shank are reacted by the bore 182. The retaining sleeve 164 is laser welded or otherwise attached to the output shaft 160 to effectively operate as a single, integral unit. Additional features of the retaining sleeve 164 are described further below with reference to FIG. 4.

Figure 3:
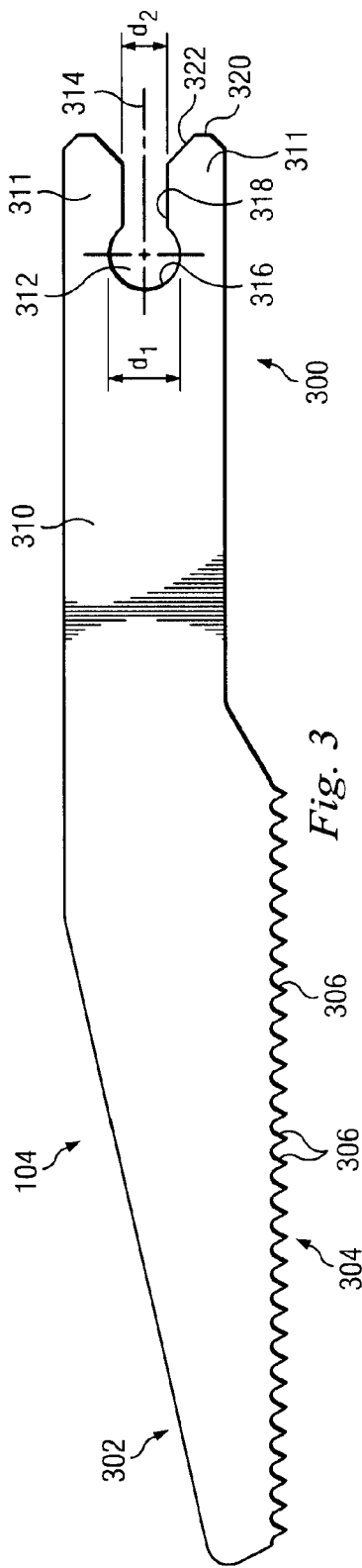
FIG. 3 is an illustration of an exemplary cutting tool from the reciprocating bone-cutting surgical system of FIG. 1 according to one exemplary aspect of the present disclosure.

For ease of explanation, the cutting tool 104 will be described before continuing with the description of the surgical saw. FIG. 3 shows an exemplary cutting tool 104 usable with the surgical saw 102 in FIG. 1 and securable with the blade retaining mechanism 110. Here, the cutting tool is formed of a single, monolithic material that may be stamped or cut from a metal sheet or flat material. As such, the cutting tool comprises two planar, parallel sides. The cutting tool 104 includes a proximal portion 300 that that facilitates interconnection with the blade retaining mechanism 110 and a distal portion 302 having a cutting edge 304 including a plurality of cutting teeth 306 formed thereon. In this example, the cutting edge 304 is disposed along a lateral side of the cutting tool 104.

Figure 8:
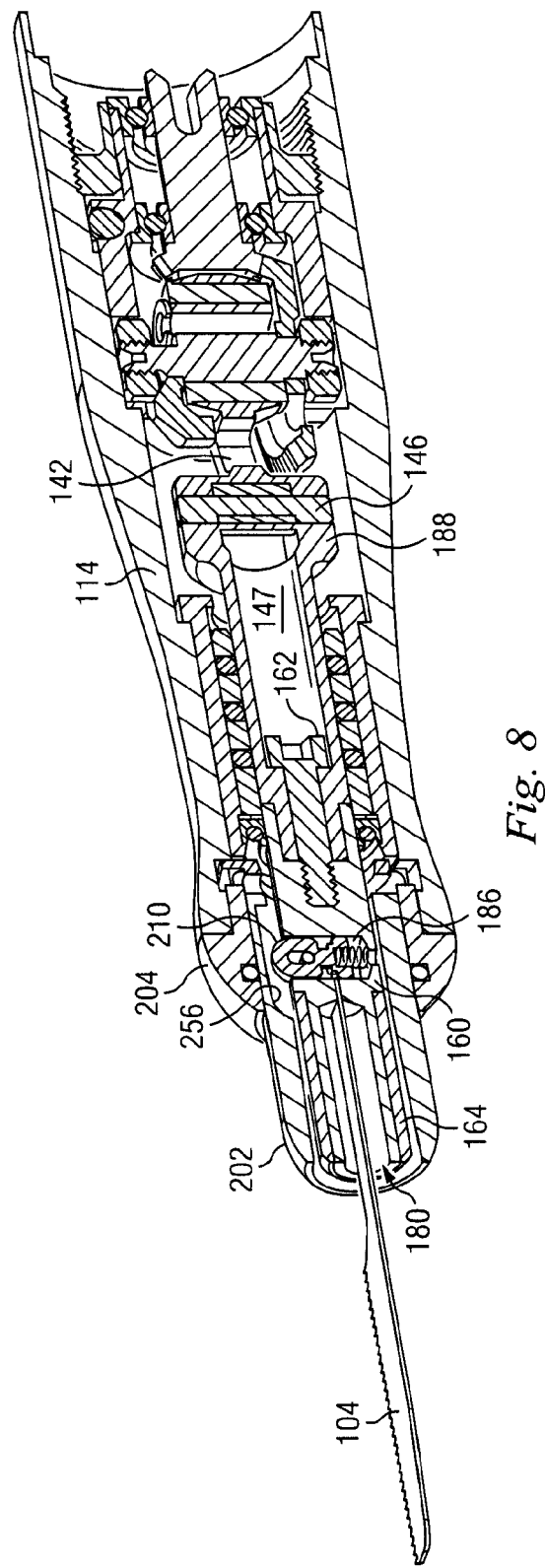
FIG. 8 is an illustration of a longitudinal cross-section of the reciprocating bone-cutting surgical system of FIG. 1 in a retracted condition according to one exemplary aspect of the present disclosure.

In this example, the proximal portion 300 is defined by a shank 310 that includes a slot 312 extending inwardly along a longitudinal axis 314 from the proximal portion 300 of the cutting tool 104. The slot 312 divides the proximal portion 300 into two parallel, proximally-projecting arms 311. As shown, the slot 312 is shaped as key-hole with a wider portion 316 and a narrower portion 318. In this embodiment, the narrower portion 318 is proximal of the distal wider portion 316. Here, the wider portion 316 is circular shaped, while the narrower portion intersects the circular shape with substantially straight longitudinal edges. The transverse distance d2 measured between the longitudinal edges is less than the distance d1 of the circular portion as shown in FIG. 8. The narrower portion extends substantially to a proximal end 320 of the cutting tool 104. In the example shown, the narrower portion 318 intersects with the proximal end 320 of the cutting tool at a funnel-like opening 322 defined by substantially straight edges 318 facing at angle toward the longitudinal axis 314. The straight edges may help guide the cutting tool 104 into place on the blade retaining mechanism 110.

Figure 4:
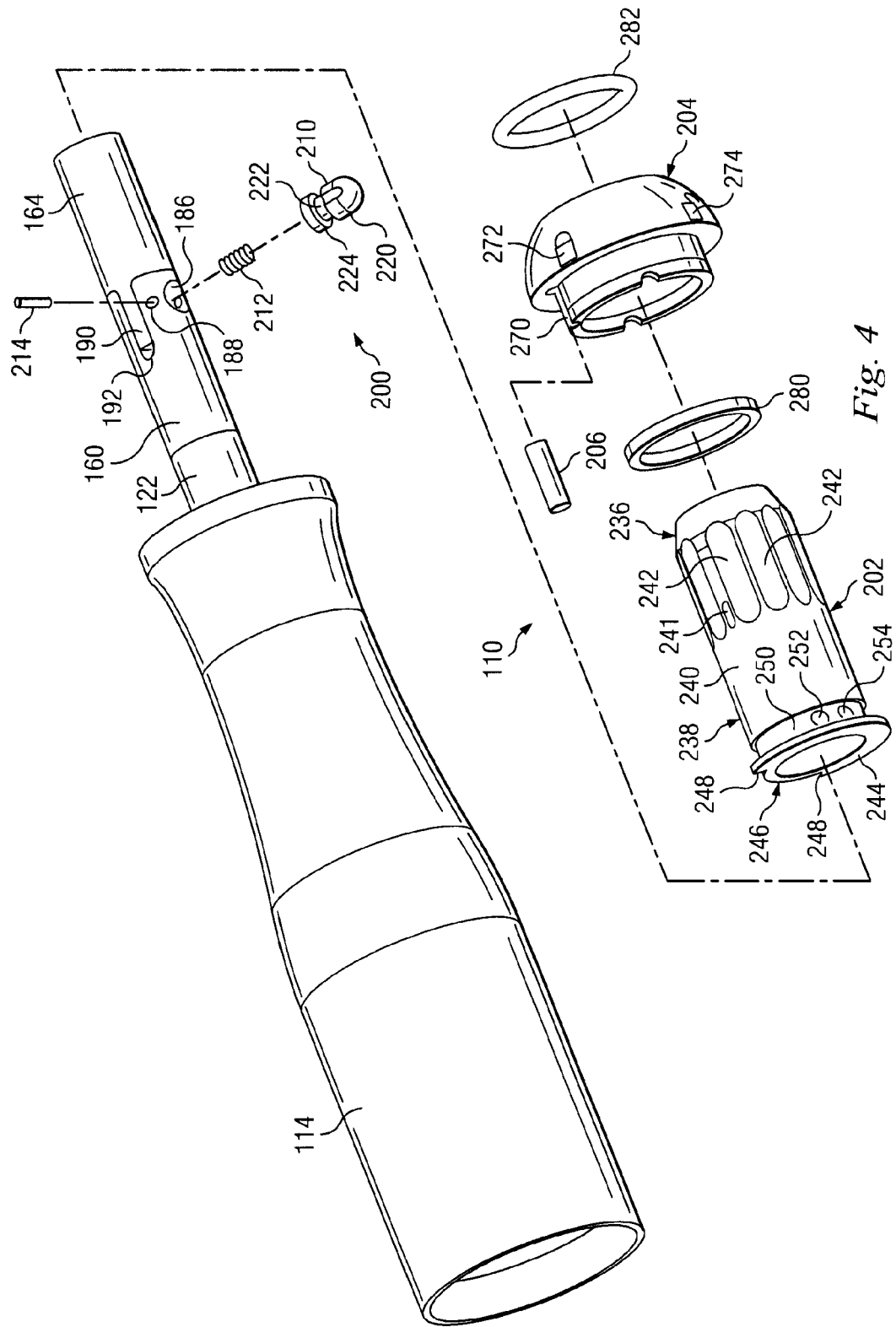
FIG. 4 is an illustration of an exploded blade retaining mechanism from the reciprocating bone-cutting surgical system of FIG. 1 according to one exemplary aspect of the present disclosure.

Returning now to the surgical saw, the blade retaining mechanism 110 will now be described. The blade retaining mechanism 110 is configured to connect the cutting tool 104 to the surgical saw 102 simply and securely, while shielding reciprocating elements from the user. The blade retaining mechanism 110 is shown in FIG. 4 in exploded form. It includes the output shaft 160 with the retaining sleeve 164, a locking mechanism 200, an actuator knob 202, a cap 204, and a stop pin 206. FIG. 4 shows the transverse hole 186 in the output shaft 160. Adjacent the transverse hole 186, the output shaft 160 includes a pin-hole 188 that intersects the transverse hole 186.

As can be seen, the output shaft 160, with the retaining sleeve 164 disposed about its distal end, projects from the drive housing 114. The retaining sleeve 164 in this example includes two opposing projecting portions 190 (only one is shown in FIG. 4) configured to be received into corresponding slots 192 (only one is shown in FIG. 4) in the output shaft 160. Here, the slots 192 align radially with the slots 184 formed in the output shaft 160.

The locking mechanism 200 is disposable in the transverse hole 186 and includes a lock pin 210, a lock spring 212, and a pin stop 214. The lock pin 210 is configured to displace relative to the transverse hole 186. It is also shown in cross-section in FIG. 5. The lock pin 210 includes a round upper portion 220, a neck 222, and a lower portion 224. The upper portion 220 includes rounded top engagement surface 221 and a through slot 226 extending therethrough that receives the pin stop 214.

The neck 222 is a narrow portion between the upper and lower portions 220, 224. In the embodiment shown, it has a circular diameter. However, in some embodiments, the neck 222 is narrow on only two transverse sides. The neck 222 is sized to fit between the parallel projecting arms 311 on the cutting tool 104 or on other surgical tools. As such, it has a diameter or transverse width less than the width d2 in FIG. 3. Therefore, when the neck 222 is aligned with the slots 184 in the output shaft 160 (when the actuator knob is rotated to the unlocked position), the cutting tool 104 may be inserted and removed from the surgical saw 102 because the projecting arms 311 of the cutting tool can slide past on either side of the neck 222.

Figure 5:
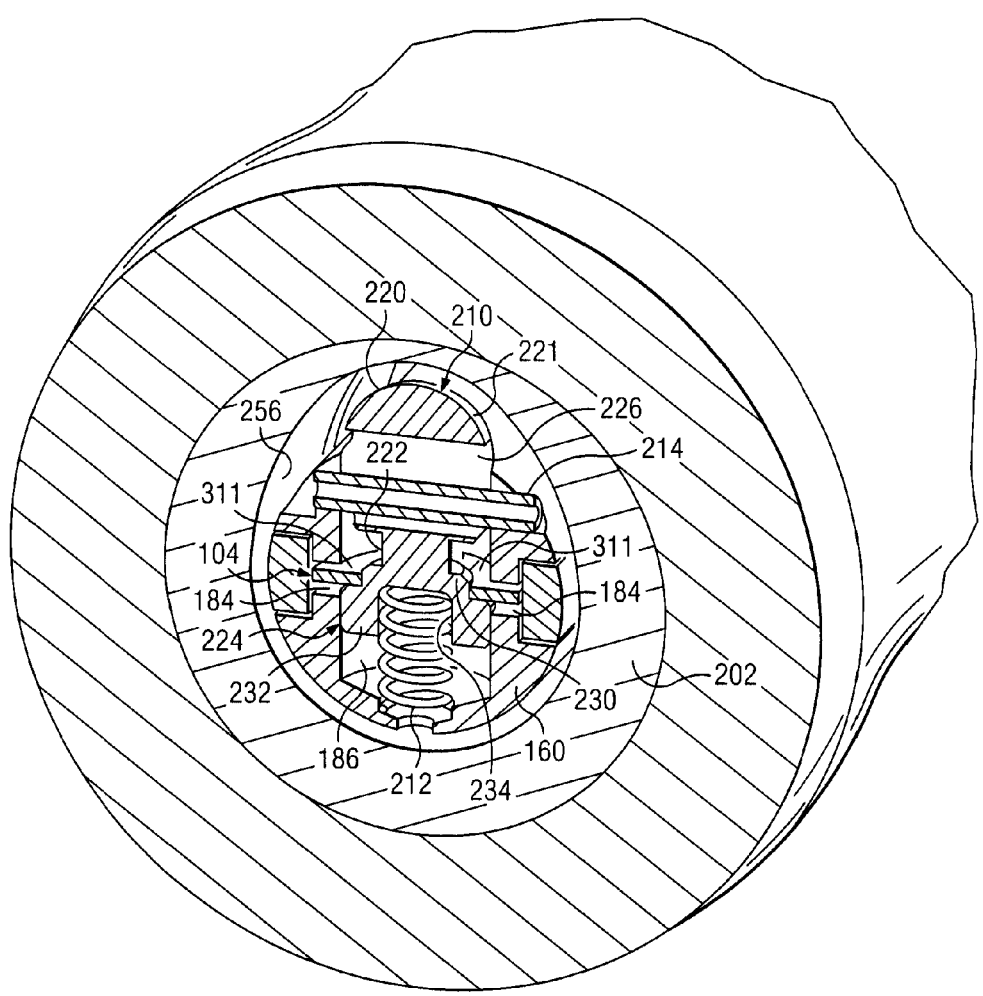
FIG. 5 is an illustration of a traverse cross-section of a portion of the blade retaining mechanism of the reciprocating bone-cutting surgical system of FIG. 1 according to one exemplary aspect of the present disclosure.

The lower portion 224 includes a first tier 230 having a first diameter and a second tier 232 having a second diameter. The diameter (or width) of the first tier 230 is sized to correspond with the wider portion 316 of the cutting tool 104 in FIG. 3. Accordingly, the diameter (or width) of the first tier 230 is greater than the distance d2 in FIG. 3. As can be seen in FIG. 4, the first tier 230 is disposed between the projecting arms 311 of the cutting tool 104. The second tier 232 has a diameter or width sized larger than the wider portion 316 between the parallel projecting arms 311 on the cutting tool 104. This can be seen in FIG. 5, where the second tier 232 is configured to abut against, but not pass between the two projecting arms 311 on the cutting tool 104. The lower portion 224 also includes a receiving bore 234 formed therein that receives the lock spring 212. The lock spring 212 also engages the bottom of the transverse hole 186 and provides a biasing force to bias the lock pin 210 to a tool locked position in the output shaft 160. Here, the tool lock position is where the first tier 230 is disposed in the wider portion 316 of the cutting tool. The tool unlock position is where the neck 222 is disposed in the wider portion 316 of the cutting tool 104. In FIG. 5, the cutting tool 104 is in the tool lock position because the first tier 230 of the bottom portion 224 is disposed between the projecting arms 311 of the cutting tool 104 preventing its removal. Because the first tier width is greater than the distance d2, the first tier 230 mechanically prevents removal of the cutting tool 104. In addition, since the lateral edges of the cutting tool 104 extend into the slots 184 on each side of the transverse hole 186, the arms 311 of the cutting tool are trapped between the boundary of the slots 184 and the second tier 232, biased against the cutting tool 104.

In FIG. 5, the pin stop 214 extends through the through slot 226 in the lock pin 210, and into the output shaft 160. Since it is secured in place in the pin hole 188 (FIG. 4), the lock pin 210 may move up and down within the transverse hole 186, but cannot be removed from the transverse hole 186. That is, the pin stop 214 limits the range of the travel of the lock pin 210, preventing its removal from the transverse hole 186. As can be seen the lock spring 212 biases the lockpin 210 toward a locked position.

The actuator knob 202 will be described with reference to FIGS. 2 and 4-7. The actuator knob 202 is rotatable relative to the drive housing 114 about the longitudinal axis, and is used to change the surgical saw between a tool lock position and a tool unlocked position, or a release position. In the tool lock position, the cutting tool 104 is secured in the surgical saw 102 and cannot be removed. In the tool unlock position, the cutting tool 104 may be removed from or a new tool may be inserted into the surgical saw 102. In this embodiment, the actuator knob 202 is axially fixed relative to the drive housing 114 and does not move with the reciprocating elements of the surgical saw 102. Accordingly, the actuator knob 202 may shield users or the patient from inadvertent contact with reciprocating elements of the surgical saw 102, such as the output shaft 160.

The actuator knob 202 has a distal portion 236 and a proximal portion 238. An outer surface 240 includes gripping features 242, shown as a series of longitudinally extending indentations. In addition, the outer surface 240 includes reference indicia 241 disposed to mark the relative position of the actuator knob 202 and indicate whether the blade retaining mechanism 110 is in a locked or unlocked condition.

The proximal portion 238 of the actuator knob 202 includes a flange 244 extending, in this embodiment, three quarters or 270 degrees about the actuator knob 202. Accordingly, in this embodiment, the flange 244 includes a 90 degree cutout 246 in the flange 244. The edges of the flange 244 at the cutout 246 define stop surfaces 248, as will be described further below.

A radial recess 250 adjacent the flange 244 includes pockets 252 operable as a portion of a detent that provides users with tactile feedback when rotating the actuator knob 202. In this embodiment, the actuator knob 202 includes four pockets 252 that cooperate with detent balls (not shown) disposed in the drive housing 114 in a manner known in the art. In addition to the pockets 252, the radial recess 250 includes one or more windows 254 that aid in the communication of steam passages during the steam sterilization processes.

The actuator knob 202 has an inner passage formed by two portions. As can be seen in FIG. 2, the distal portion 236 of the actuator knob 202 includes a substantially cylindrical inner surface 255, while the proximal portion 238 of the actuator knob 202 includes a cam-shaped interior surface 256. A cross-section of the cam-shaped interior surface 256 is shown in FIG. 5. The cam shaped interior surface 256 is configured to interface with the engagement surface 221 of the lock pin 210. Since the actuator knob can 202 be rotated about the longitudinal axis, the cam surface 256 can rotate relative to the drive shaft 160, and the corresponding locking mechanism 200. Its rotation causes a portion of the inner surface of the cam surface 256 to engage against and radially displace the lock pin 210 deeper into the transverse hole 186, compressing the lock spring 212. This displacement moves the lockpin 210 from its locked position with the lower portion 224 engaging or otherwise preventing removal a cutting tool 104 to its unlocked position, where the neck 222 is aligned with the slots 184 and the cutting tool 184 can be inserted or removed. FIG. 5 shows the cam surface aligned in the locked position, where the lock pin 210 is able to project from the output shaft 160 and the lower portion 224 of the lock pin 210 is engaged with the cutting tool 104.

Figure 6:
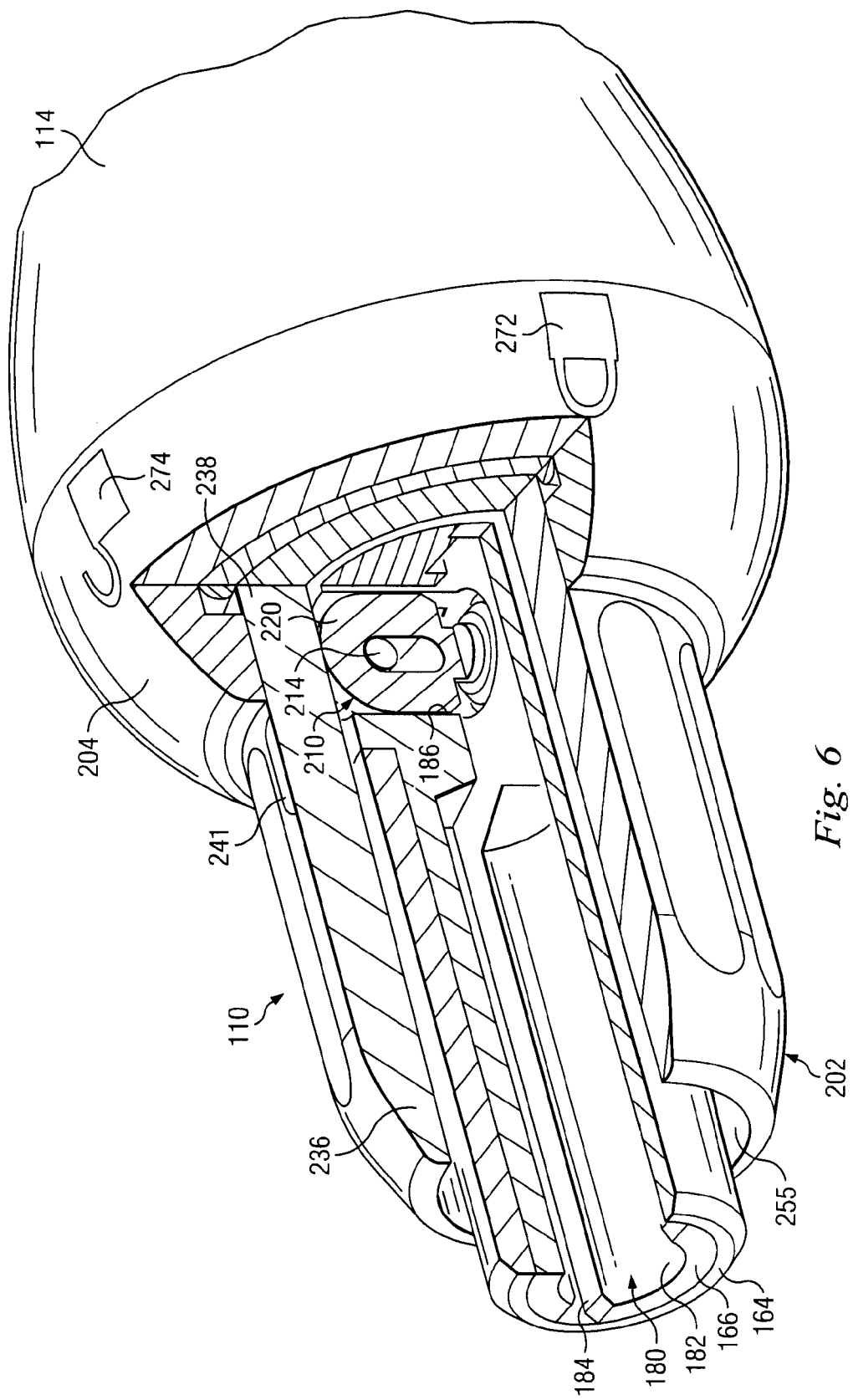
FIGS. 6 and 7 are partial cross-sectional views showing a portion of the blade retaining mechanism of the reciprocating bone-cutting surgical system of FIG. 1 according to one exemplary aspect of the present disclosure.
Figure 7:
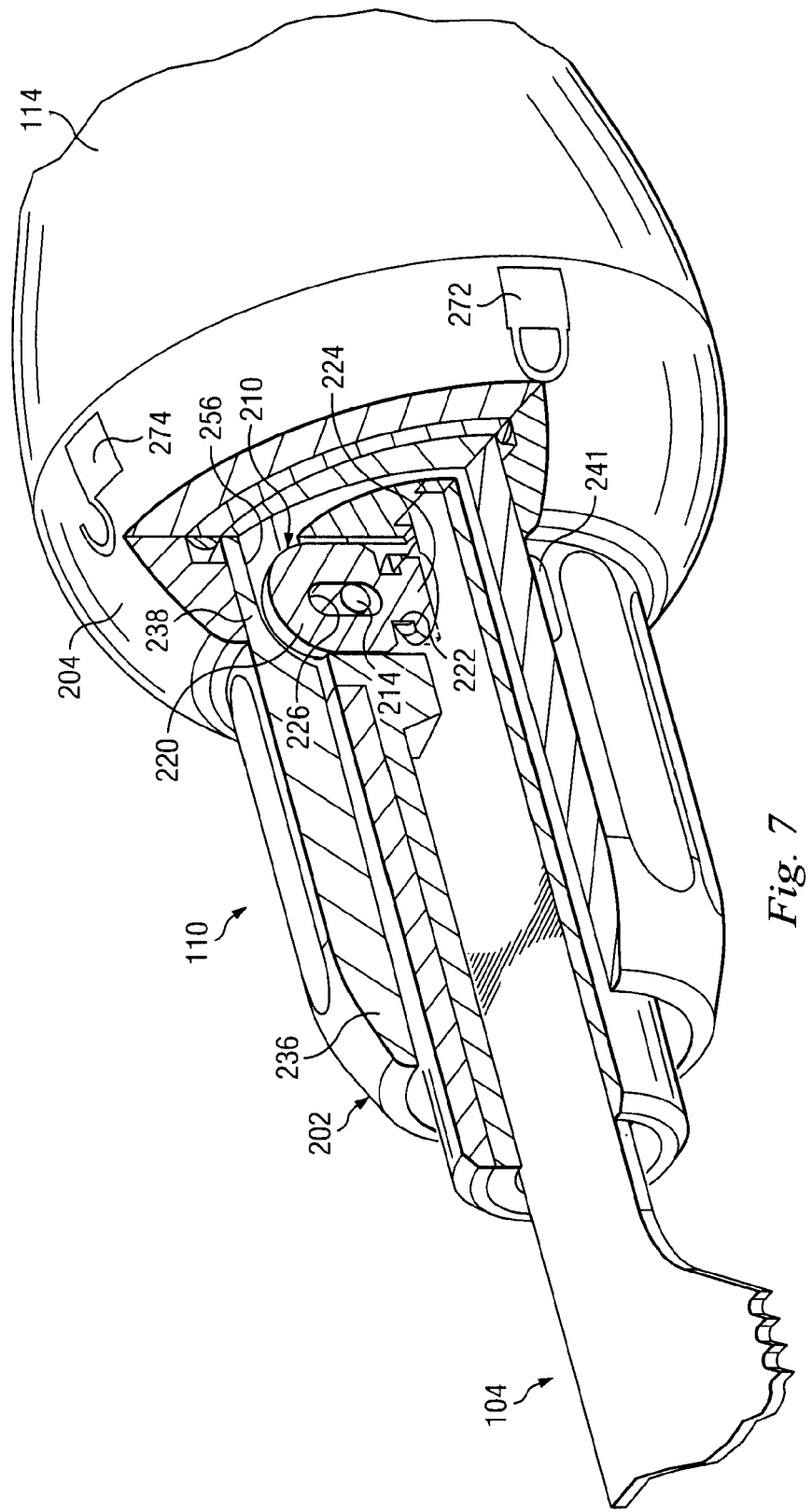

The cap 204 is best seen in FIGS. 4, 6, and 7 and is configured to connect to and be fixed in place relative to the drive housing 114. In the example shown, the cap 204 includes a rounded distal end and a proximal portion that projects into the drive housing 114. As best seen in FIG. 4, the cap 204 includes a pin receiving slot 270 formed in one side. The pin receiving slot 270 is disposed radially inward from the exterior of the cap 204, so that the stop pin 206, shown as a pin, in the receiving slot 270 can be retained inside the cap 204 and the drive housing 114. In this example, the cap 204 has an outer diameter sized to match that of the drive housing 114. In this example, a first reference indicium shown as a lock indicium 272 representing a locked position and a second reference indicium shown as an unlock indicium 274 representing an unlocked condition are disposed on the outer surface of the cap 204. These reference indicia are disposed to correspond to a position of the actuator knob 202 with its indicium 241 and indicate whether the blade retaining mechanism 110 is in a locked or unlocked condition. In this example, the reference indicia 272, 274 are spaced 90 degrees apart, indicating that the actuator knob 202 is a quarter-turn (90 degree turn) element to change from the locked position to the unlocked position or the unlocked position to the locked position.

Still referring to FIGS. 2 and 4, the surgical saw 102 includes a lip seal 280 and an o-ring 282. The lip seal 280 is disposed in contact with the drive shaft 160, and the o-ring 282 is disposed in contact with the actuator knob 202.

The stop pin 206, shown in FIG. 4, is disposed in the pin receiving slot 270 in the cap 204 and in the drive housing 114. The stop pin 206 is aligned adjacent the actuator knob 202, and extends through the cutout 246. When the actuator knob 202 is rotated, the flange ends 248 adjacent the cutout 246 engages the stop pin 206 and mechanically prevents additional rotation of the actuator knob 202. Accordingly the cutout 246 is aligned with the stop pin 206 so that the rotation of the actuator knob 202 occurs between the locked and unlocked position.

In the example shown, the cutout 246, the indicia 241, and the cam surface 256 are all configured so that the locked condition and the unlocked condition are a quarter turn or 90 degrees apart. However, in other examples, the range of rotation is selected to be different than 90 degrees. In one example the range of rotation is greater than 90 degrees, and in one embodiment is within a range of 190 and 110 degrees. Other ranges, both larger and smaller are contemplated and can be arranged by adjustment of the flange cutout 246, the inner cam surface 256, and other components.

FIG. 6 shows a partial cross-sectional view of the blade retaining mechanism 110 in an unlocked position without a cutting tool, and FIG. 7 shows the blade retaining mechanism 110 in a locked position with the cutting tool 104. As can be seen in FIG. 6, the marking indicium 241 on the actuator knob 202 is aligned with the unlock indicia 274 on the cap 204. As such, the actuator knob 202 is rotated so that the cammed inner surface 256 is engaged with the engagement surface 221 of the upper portion 220 of the lock pin 210, and the lockpin 210 is pressed into the transverse hole 186. This aligns the neck 222 with the slots 184 so that a cutting tool introduced into the tool receiving opening 180 can advance past the narrow neck 222. With the cutting tool inserted beyond the neck 222, the actuator knob 202 may be rotated from the unlocked position in FIG. 6 to the locked position in FIG. 7.

FIG. 7 shows the marking indicium 241 on the actuator knob 202 aligned with the unlock indicium 274 on the cap 204. As such, the actuator knob 202 is rotated so that the cammed inner surface 256 is spaced away from the engagement surface 221 of the upper portion 220 of the lock pin 210. As this occurs, the lock spring (FIG. 2) displaces the lockpin 210 from the depressed position to a position where the lower portion 224 engages the cutting tool 104. In this example, the first tier 230 of the lower portion 224 extends into the wider portion 316 of the slot 312 in the cutting tool 104 and the second tier 232 engages and contacts the bottom surface of the cutting tool 104. The first tier 230 prevents removal of the cutting tool 104 from the surgical saw 102 as explained above. Here, only the distal end portion of the cam surface 256 is shown in FIG. 7. However, as shown in FIG. 2, the cam surface 256 extends proximally. This ensures that even while the output shaft 160 reciprocates with the protruding lock pin 210 extending up out of the transverse hole 186, the lock pin 210 is not inadvertently displaced in a manner that will release the cutting tool.

FIG. 8 is a cross-sectional view similar to FIG. 2 with the components of the surgical saw 102 in a retracted position during a reciprocating cycle. As can be seen, the output shaft 160 reciprocates in a forward and rearward direction relative to the actuator knob 202. The retaining sleeve 164, which is fixedly connected to the yoke 122 also reciprocates. However, in this example, the components manipulated by the user, such as the actuator knob 202 do not reciprocate. Because of this, the actuator knob 202 may shield the surgeon and the patient from the reciprocating output shaft 160. In addition, by forming the reciprocating knob 202 and the mating features of the retaining components to be axially fixed relative to the drive housing 114, the mass of the reciprocating portion is reduced. This may reduce vibration during operation, resulting in improved ergonomics for the surgeon.

Figure 9:
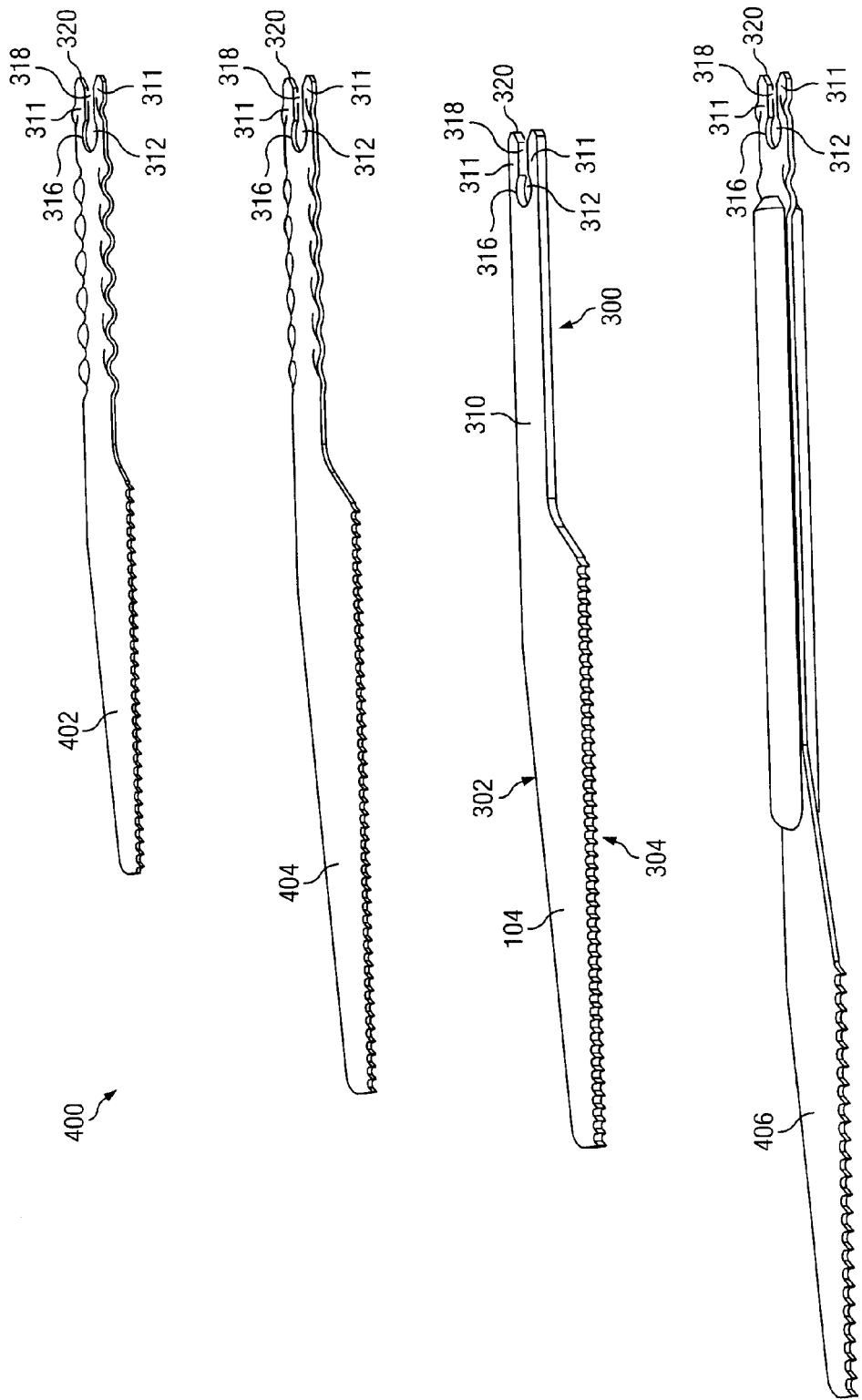
FIG. 9 is an illustration of an exemplary cutting tool set usable with a surgical saw of the reciprocating bone-cutting surgical system of FIG. 1 according to one exemplary aspect of the present disclosure.

FIG. 9 shows an exemplary tool set 400 having a plurality of cutting blades shown as saw blades usable with the blade retaining mechanism 110 disclosed herein. Here, the tool set 400 includes blades 402, 404, 104, and 406. The cutting tool 104 was described above with reference to FIG. 3. For ease of explanation, blade features similar to those of cutting tool 104 will be described with similar reference numbers. Further, some features, such as the distal portion and the teeth will not be further described here. Each of blades 402, 404, 406, like cutting tool 104, has a proximal portion 300 that that facilitates interconnection with the blade retaining mechanism 110. The proximal portion 300 is includes the slot 312 extending inwardly from the proximal end of the cutting tool 402, 404, 406. The slot 312 divides the proximal portion 300 into two parallel, proximally-projecting arms 311. In the embodiments shown, the slot 312 is shaped as key-hole with a wider portion 316 and a narrower portion 318. The transverse distance d2 measured between the longitudinal edges is less than the distance d1 of the circular portion as shown in FIG. 8. The narrower portion extends substantially to a proximal end 320 of the cutting tool 104. In the example shown, the narrower portion 318 intersects with the proximal end 320 of the cutting tool at a funnel-like opening 322.

Figure 10:
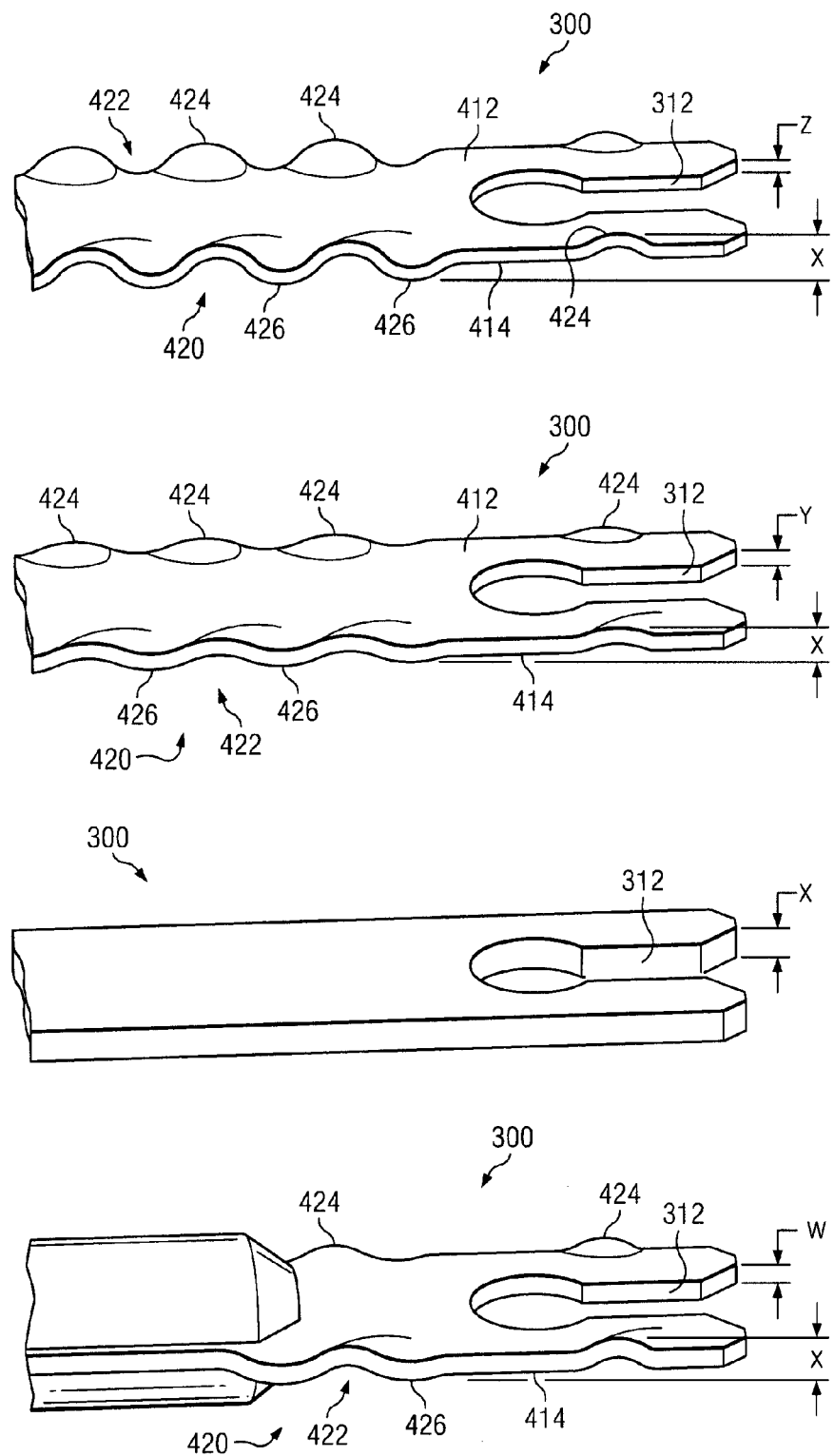
FIG. 10 is an illustration of a proximal portion of the cutting tools of FIG. 9 according to one exemplary aspect of the present disclosure.

In this blade set 400 however, the thickness of the blades of the tool set 400 varies across blades. FIG. 10 shows the proximal portions 300 of the plurality of blades 400 for simple comparison. Each of the tools 402, 404, 104, 406 includes an upper facing flat surface 412 and a lower facing flat surface 414. In this example, the blade 402 includes has a blade thickness Z measured between the flat surfaces 412, 414, the blade 404 has a blade thickness Y, the blade 104 has a blade thickness X, and the blade 406 includes a cylindrical shank 410 that ends in a flat blade having a blade thickness W. Cylindrical shank type tools may be available in varying blade thickness for surgeon preference with respect to kerf width, flexibility, etc. In this example, the blade thickness X is selected to fit within the tool receiving opening 180 and slide along the slots 184 with the most desirable fit. That is, the thickness X is selected to have a desired level of clearance in the slots for blade change-over, while at the same time minimizing the amount of excess clearance between blade 104, 402, 404, 406 and shaft 160. Minimizing excess clearance may result in less undesirable blade movement during cutting, resulting in a cleaner more accurate cut. This in turn results in a better patient outcome.

Each of the blades 104, 402, 404, 406 having a particular thickness may be utilized during different aspects of a procedure or may have different advantages or disadvantage for a particular surgical technique or procedure. However, in order to obtain consistency by minimizing undesirable blade movement, the blade shanks in each of the blades 402, 404, and 406 are deformed to create an effective thickness that matches the thickness X.

In the example shown, for example, although blade 402 has a thickness Z measured between the flat upper surface and the flat lower surface, the lateral edges of the shank 412 include a plurality of intermittent thickness enhancing features 420 shown as a deformed portion that results in a thickness X. For example, the deformed portion may comprise a plurality of embossments 422 alternating between peak high points 424 creating a point of greatest elevation from the upper flat surface 412 and a peak low point 426 of lowest elevation from the lower flat surface 414, where the distance between the high point 424 and the low points 426 match the thickness X. In the example shown the embossments 422 form a wave shape that appears as a sinusoidal embossment. The embossments 422 are formed by bending the material. This may be accomplished using, for example, a stamping or a forging process. Other processes also may be used.

Blades 402 and 406 are similarly deformed to provide an effective thickness X to correspond with a desired blade thickness for the blade retaining mechanism 110. While shown with embossments only on the lateral edges of the shank, the embossments in some embodiments extend laterally across the shank. In addition as can be seen, each of the blades 402, 404, and 406 have embossments or deformations proximal of the distal end of the slot 312. In examples where the embossments extend laterally across the shank, the flat surfaces are defined by the distal end of the cutting tools, where the cutting blade has flat parallel sides.

The cylindrical shank 410 of cutting tool 406 is compatible with the surgical saw 102 by virtue of the cylindrical bore 182 in the output shaft 160. In addition, since the proximal portion 300 is flat, the cutting tool 406 also is compatible with the remaining components of the blade retaining mechanism 110, and may be maintained in the surgical saw by the locking mechanism 200.

Figure 11:
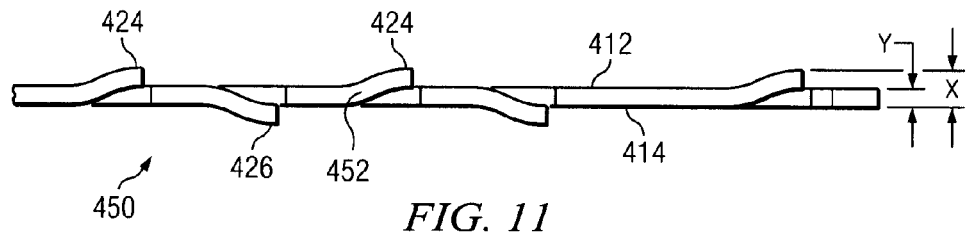
FIGS. 11-12 are illustrations of another embodiment of a proximal portion of an additional cutting tool according to one exemplary aspect of the present disclosure.
Figure 12:
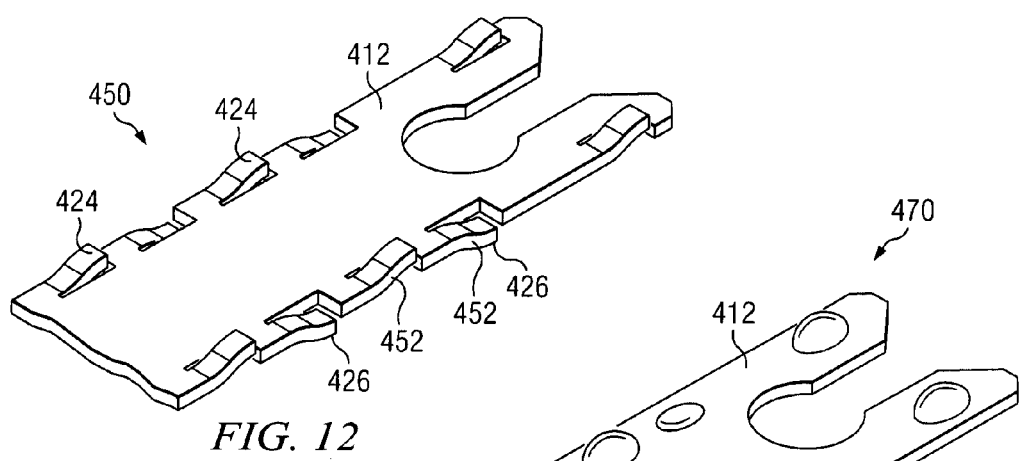
Figure 14:
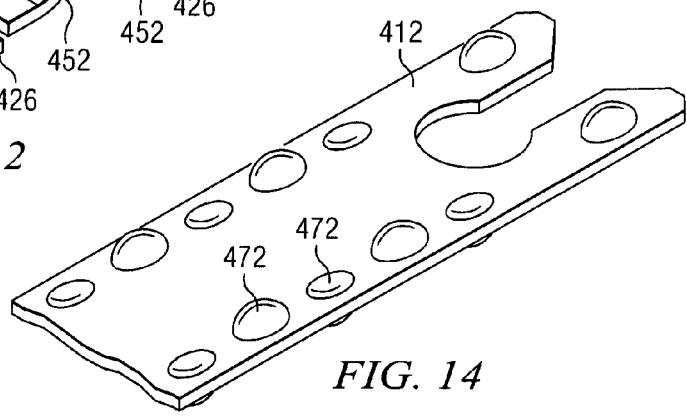
FIGS. 13-14 are illustrations of another embodiment of a proximal portion of an additional cutting tool according to one exemplary aspect of the present disclosure.
Figure 13:
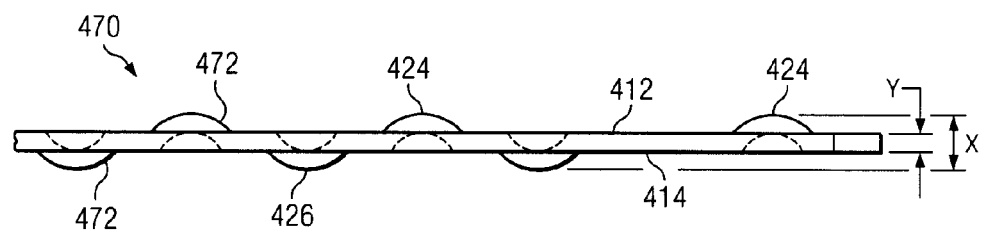
Figure 15:
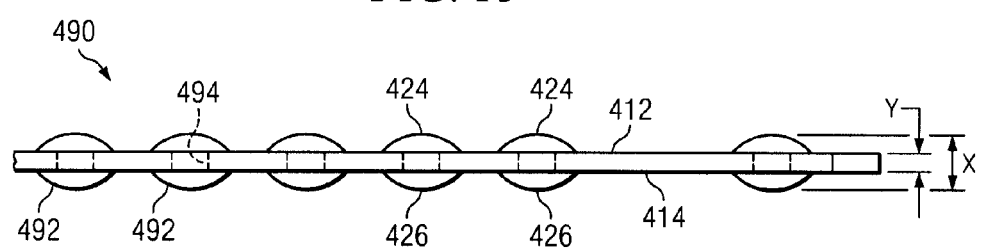
FIG. 15 is an illustration of another embodiment of a proximal portion of an additional cutting tool according to one exemplary aspect of the present disclosure.

FIGS. 11-15 show alternative intermittent thickness enhancing features. FIGS. 11 and 12 show a cutting tool 450 with deformed portions of alternating upper stamped fingers and lower stamped fingers 452. The alternating high points 424 and low points 426 on the stamped fingers 452 match the thickness X as described above. FIGS. 13 and 14 show a saw blade 470 with alternating embossed dimples 472 where the high points 424 and the low points 426 on the dimples 472 match the thickness X. FIG. 15 shows a side view of a cutting tool 490 with molded bumps 492 where the high points 424 and low points 426 on the molded bumps 492 match the thickness X. This embodiment includes a plurality of through holes 494 on the shank of the cutting tool 490. The molding material extends through the holes 494 to form the bumps 492 on both sides of the cutting tool 490, giving it a desired effective thickness. In another embodiment, the intermittent thickness enhancing features are laminated segments, such as laminated flat sections disposed on the proximal portions of the blades.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

We claim:

1. A surgical system for cutting bone and tissue of a patient, comprising:
   an outer housing;
   a reciprocating assembly disposed in the outer housing, the reciprocating assembly being structurally configured to carry a cutting tool in a reciprocating motion, the reciprocating assembly including an output shaft having a central cylindrical bore, two longitudinal flat slots on opposing sides of the cylindrical bore and a transverse hole extending through the longitudinal flat slots;
   an actuator knob manually accessible to the user, the actuator knob being fixed axially to the outer housing, the reciprocating assembly reciprocating relative to the actuator knob, the actuator knob being configured for rotational movement between a lock position and an unlock position; and
   a locking mechanism configured to retain a cutting tool within the reciprocating assembly, the locking mechanism being responsive to movement of the actuator knob to maintain the tool within the output shaft when the actuator knob is in the lock position and permit removal of the tool when the actuator knob is in the unlock position, the locking mechanism including a lock pin moveable in the transverse hole and having a narrow neck portion configured to be aligned with the longitudinal flat slots in the unlock position.

2. The surgical system of claim 1, wherein the lock pin is moveable in a direction transverse to the direction of the reciprocating motion when the actuator knob rotates between a lock position and an unlock position, and wherein the lock pin is biased in the lock position by a lock spring received in a bore of the lock pin.

3. The surgical system of claim 2, wherein the actuator knob comprises an inner cam surface, the inner cam surface being configured to engage and displace the lock pin upon rotation of the actuator knob.

4. The surgical system of claim 1, wherein the actuator knob comprises an inner surface shaped as a cam.

5. The surgical system of claim 1, wherein the cylindrical bore is sized and arranged to receive a cutting tool having a cylindrical shank and wherein the longitudinal flat slots are sized and arranged to receive a cutting tool having a flat shank.

6. The surgical system of claim 1, wherein the actuator knob comprises a flange rotatable relative to the outer housing, the flange having a cutout formed therein the cutout being disposed to engage a stop element associated with the housing in a manner that limits a range of rotation of the actuator knob.

7. The surgical system of claim 1, wherein the actuator knob comprises a distal portion and a proximal portion, the distal portion having a cylindrical inner surface and the proximal portion having a cam inner surface.

8. The surgical system of claim 1, wherein the locking mechanism is configured to reciprocate with the reciprocating assembly.

9. The surgical system of claim 1, wherein the reciprocating assembly comprises a retaining sleeve disposed about the output shaft, and a yoke rigidly connected to the output shaft.

10. The surgical system of claim 1, comprising a cutting tool receivable in the output shaft and shaped to be carried by the reciprocating assembly, the cutting tool having a proximal end configured to selectively engage the locking mechanism, the cutting tool having a flat proximal portion divided into longitudinal extending arms extendable on either side of the locking mechanism.

11. A surgical system for cutting bone and tissue of a patient, comprising:
   an outer housing;
   a reciprocating assembly disposed in the outer housing, the reciprocating assembly being structurally configured to carry a cutting tool in a reciprocating motion, the reciprocating assembly including an output shaft having a central cylindrical bore, two longitudinal flat slots on opposing sides of the cylindrical bore and a transverse hole extending through the longitudinal flat slots;
   a locking mechanism configured to retain a cutting tool within the output shaft, the locking mechanism being displaceable in a direction transverse to the direction of the reciprocating motion and being structurally configured to engage the tool in a first position and to be disengaged from the tool in a second position, the locking mechanism including a lock pin movable within the transverse hole and having a narrow neck portion configured to be aligned with the longitudinal flat slots in the unlock position; and
   an actuator knob manually accessible to the user and disposed about the reciprocating assembly, the actuator knob being fixed axially to the housing and being rotatable relative to the housing, the actuator knob having an inner cam surface configured to selectively engage the locking mechanism and displace the locking mechanism from the first position to the second position, the inner cam surface extending axially in the longitudinal direction to accommodate the reciprocating motion of the locking mechanism.

12. The surgical system of claim 11, wherein the lock pin includes:
   a first portion configured to engage with the inner cam surface of the actuator knob;
   a second portion configured to engage a side of a cutting tool disposed within the output shaft of the reciprocating assembly, the second portion including a bore receiving a lock spring therein configured for biasing the lock pin in the lock position; and
   wherein the neck portion is disposed between the first and second portions, the neck portion having a transverse width smaller than a transverse width of the second portion to permit insertion and removal of the tool.

13. The surgical system of claim 11, comprising a cutting tool receivable in the output shaft and shaped to be carried by the reciprocating assembly, the cutting tool having a proximal end configured to selectively engage the locking mechanism, the cutting tool having a flat proximal portion divided into longitudinal extending arms extendable on either side of the locking mechanism.

14. A surgical system for cutting bone and tissue of a patient, comprising:
   an outer housing having a longitudinal axis;
   a reciprocating assembly disposed in the outer housing, the reciprocating assembly being structurally configured to carry a cutting tool in a reciprocating motion, the reciprocating assembly having an output shaft with a cutting tool receiving opening including a central cylindrical bore, two longitudinal flat slots on opposing sides of the cylindrical bore and a transverse hole extending through the longitudinal flat slots;
   an actuator knob manually rotatable relative to the outer housing about the longitudinal axis and axially fixed to the outer housing, the reciprocating assembly reciprocating relative to the actuator knob, the actuator knob rotatable between a lock position for the cutting tool and an unlock position for the cutting tool; and
   a lock pin associated with the reciprocating assembly, the lock pin being moveable within the transverse hole in a direction transverse to the direction of the reciprocating motion when the actuator knob rotates between the lock position and the unlock position, the lock pin having a narrow neck portion configured to be aligned with the longitudinal flat slots in the unlock position.

15. The surgical system of claim 14, wherein the actuator knob comprises an inner cam surface, the inner cam surface being configured to engage and displace the lock pin upon rotation of the actuator knob.

16. The surgical system of claim 15, wherein the locking pin comprises:
   a first portion configured to engage with the inner cam surface of the actuator knob;
   a second portion configured to engage a side of a cutting tool disposed within the tool receiving opening of the reciprocating assembly; and wherein the second portion includes a bore receiving a lock spring configured for biasing the lock pin in the lock position; and wherein
   the neck portion is disposed between the first and second portions, the neck portion having a transverse width smaller than a transverse width of the second portion to permit insertion and removal of the cutting tool.

17. The surgical system of claim 14, wherein the actuator knob comprises a flange rotatable relative to the outer housing, the flange having a cutout formed therein the cutout being disposed to engage a stop element associated with the housing in a manner that limits a range of rotation of the actuator knob.

18. The surgical system of claim 14, wherein the reciprocating assembly comprises a retaining sleeve disposed about the output shaft, and a yoke rigidly connected to the output shaft.

19. A surgical system for cutting bone and tissue of a patient, comprising:
   an outer housing having a longitudinal axis;
   a reciprocating assembly disposed in the outer housing, the reciprocating assembly being structurally configured to carry a cutting tool in a reciprocating motion, the reciprocating assembly including an output shaft having a central cylindrical bore, two longitudinal flat slots on opposing sides of the cylindrical bore and a transverse hole extending through the longitudinal flat slots;
   an actuator knob manually rotatable relative to the outer housing about the longitudinal axis and axially fixed to the outer housing, the reciprocating assembly reciprocating relative to the actuator knob, the actuator knob rotatable between a lock position for the cutting tool and an unlock position for the cutting tool; and
   a locking mechanism configured to retain a cutting tool within the reciprocating assembly, the locking mechanism being responsive to movement of the actuator knob to maintain the tool within the output shaft when the actuator knob is in the lock position and permit removal of the tool when the actuator knob is in the unlock position, the locking mechanism including a lock pin moveable in the transverse hole and having a narrow neck portion configured to be aligned with the longitudinal flat slots in the unlock position, the lock pin including a bore receiving a lock spring biasing the lock pin in the lock position.

20. The surgical system of claim 19, wherein the locking mechanism includes a pin stop extending through a slot of the lock pin and into the output shaft, the stop pin configured to limit the range of travel of the lock pin.

21. The surgical system of claim 20, wherein the actuator knob comprises an inner cam surface, the inner cam surface being configured to engage and displace the lock pin upon rotation of the actuator knob.

22. The surgical system of claim 21, wherein the locking pin comprises:
- a first portion configured to engage with the inner cam surface of the actuator knob;
- a second portion configured to engage a side of a cutting tool disposed within the output shaft of the reciprocating assembly, the second portion including the bore and the lock spring; and wherein
- the neck portion is disposed between the first and second portions, the neck portion having a transverse width smaller than a transverse width of the second portion to permit insertion and removal of the cutting tool.

* * * * *